United States Patent [19]

Nathan

[11] Patent Number: 4,928,323
[45] Date of Patent: May 29, 1990

[54] GARMENTS AND PARTS THEREOF

[75] Inventor: Efraim Nathan, Philadelphia, Pa.

[73] Assignee: Lontex Corporation, Perkasie, Pa.

[21] Appl. No.: 313,403

[22] Filed: Feb. 21, 1989

[51] Int. Cl.$^5$ .............................. A41B 9/00; A41B 9/12
[52] U.S. Cl. ............................................ 2/406; 2/400; 604/385.1
[58] Field of Search .................... 2/400, 402, 403–404, 2/406, 407, 408, 78 B, 78 D; 604/385.1, 385.2, 386, 387, 393, 395

[56] References Cited

U.S. PATENT DOCUMENTS

| | | | |
|---|---|---|---|
| 1,168,679 | 1/1916 | Rutherford | 604/398 |
| 2,016,355 | 8/1935 | Alsop | 2/406 |
| 2,052,598 | 8/1936 | Berg | 604/395 |
| 2,292,030 | 8/1942 | Kraft | 2/400 |
| 2,494,292 | 1/1950 | Frazier | 604/395 |
| 2,523,079 | 9/1950 | Walter et al. | 604/394 |
| 2,591,079 | 4/1952 | Leaton | 2/402 |
| 2,638,095 | 5/1953 | Smythe | 604/398 |
| 2,705,957 | 4/1955 | Mauro | 604/395 |
| 2,890,701 | 6/1959 | Weinman | 604/394 |
| 2,977,957 | 4/1961 | Clyne | 604/396 |
| 2,985,170 | 5/1961 | Title | 604/398 |
| 3,483,864 | 12/1969 | Zacarias | 604/398 |
| 3,554,195 | 1/1971 | Murdoch | 2/402 X |
| 3,704,710 | 12/1972 | Fifer | 604/396 |
| 4,421,512 | 12/1983 | Papajohn | 604/396 |
| 4,662,877 | 5/1987 | Williams | 604/385.2 |
| 4,695,279 | 9/1987 | Steer | 2/406 X |
| 4,834,737 | 5/1989 | Khan | 604/385.2 |

FOREIGN PATENT DOCUMENTS

| | | | |
|---|---|---|---|
| 0672921 | 10/1963 | Canada | 604/395 |
| 812455 | 5/1937 | France | 2/407 |
| 2086605 | 12/1971 | France | 2/406 |
| 743365 | 1/1956 | New Zealand | 604/398 |
| 8001133 | 6/1980 | World Int. Prop. O. | 2/406 |

Primary Examiner—Werner H. Schroeder
Assistant Examiner—Jeanette E. Chapman
Attorney, Agent, or Firm—Panitch Schwarze Jacobs & Nadel

[57] ABSTRACT

Improved garments of the present invention which may be a panty, underpants, panty hose, girdle, panty girdle, swimsuit, trunk, teddy, leotard, thermal underwear and other garments which may be worn in direct contact with the crotch region, are provided with inner and outer sets of pockets or equivalent structures to receive and retain flush on the crotch area of the garment, either a removable absorbent pad of a first size, such as a typical disposable panty liner, or a removable absorbent pad of a larger size, such as a typical disposable sanitary napkin. The invention may be provided in a crotch assembly including a crotch piece and a plurality of panels which are attached to the crotch piece in a manner to form the inner and outer pairs of pockets. The assembly may be used as a panel forming the crotch of a garment or attached to the inner side of a garment having a finished crotch as a liner.

9 Claims, 2 Drawing Sheets

U.S. Patent May 29, 1990 Sheet 1 of 2 4,928,323
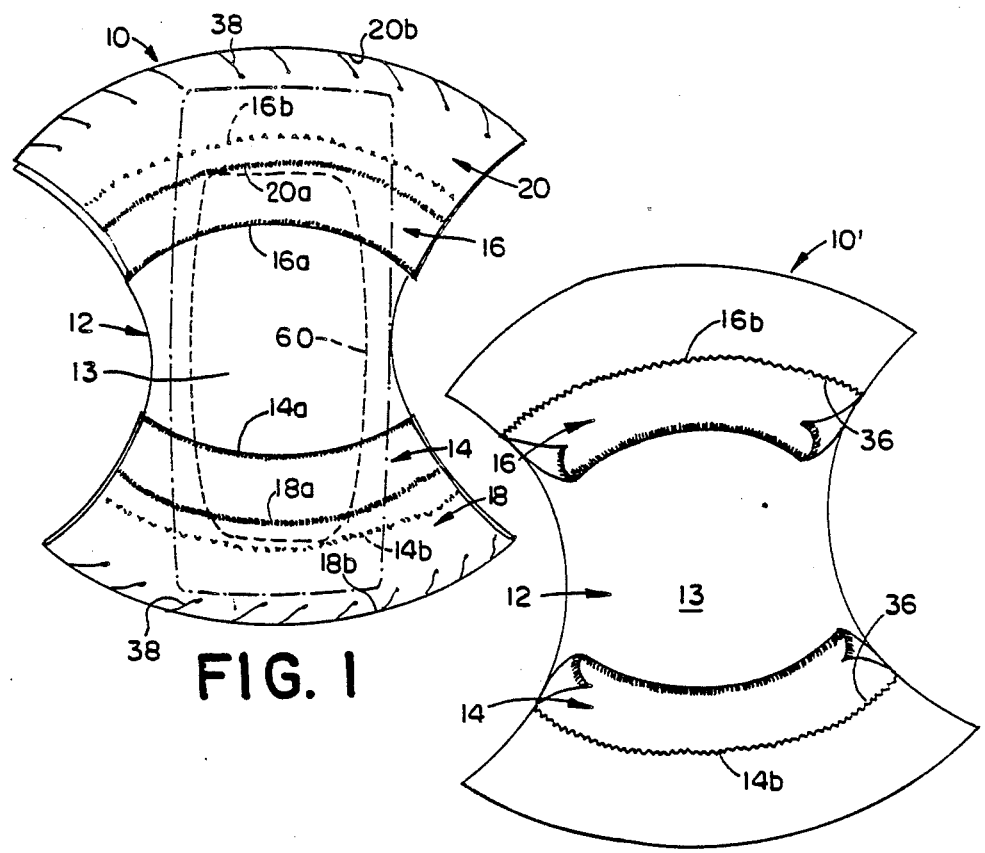
FIG. 1
FIG. 3
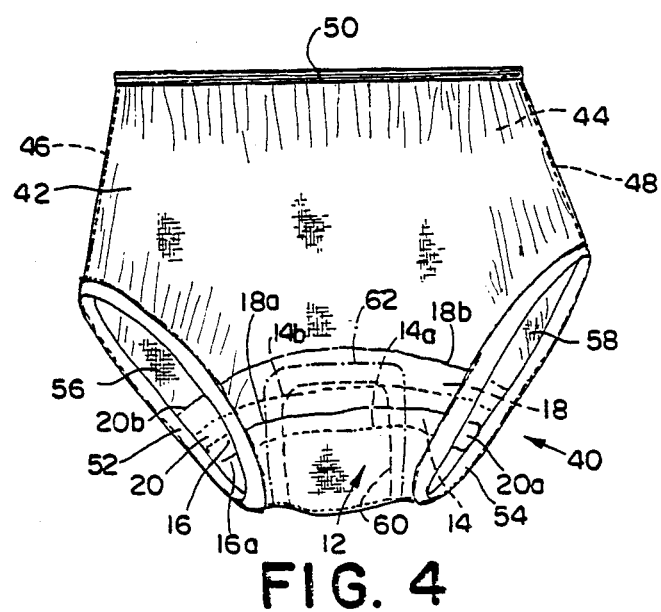
FIG. 4

GARMENTS AND PARTS THEREOF

FIELD OF THE INVENTION

This invention relates to garments and garment construction and, more specifically, to undergarments and to other garments which may be worn in direct contact with the crotch region, and parts thereof, which include absorbent pad holding arrangements for comfortably and accurately holding and positioning removable pads of various sizes in the crotch region of such garments.

BACKGROUND OF THE INVENTION

Various physical conditions such as menstruation, incontinence, etc. and medical treatments are accompanied by fluid discharge in the crotch region. The present invention is designed to overcome the difficulties previously encountered in supporting and retaining absorbent pads such as disposable panty liners, sanitary pads, surgical dressings, etc. worn in the crotch region by the user.

Various arrangements for holding one pad in the crotch area have been proposed including belt and harness devices and liners providing slots, loops or pockets to hold opposite ends of the pad. However, none have been known to securely receive and position pads of various sizes in a way to prevent either movement of smaller pads or bunching of larger pads.

SUMMARY OF THE INVENTION

In one aspect, the present invention is a garment crotch assembly comprising a fabric crotch piece having a pair of opposing, generally concave edges; inner fabric means attached to the crotch piece for receiving and retaining flush on one side of the crotch piece, extending longitudinally between the concave edges, a removable pad of up to a first size; and outer fabric means attached to the crotch piece for receiving and retaining flush on the one side of the crotch piece, extending longitudinally between the concave edges, a removable absorbent pad of a size larger than the first size.

In another aspect the invention is an improvement in a garment that includes a waistband, a crotch region configured for locating between a wearer's legs, and front and back regions each extending from the crotch region to the waistband for supporting the crotch region from the waistband, wherein the improvement comprises: inner fabric means secured to the garment for receiving and retaining flush on an inner side of the garment, extending longitudinally through the crotch region between the front and back regions, a removable absorbent pad of up to a first size and outer fabric means secured to the undergarment for receiving and retaining flush on the inner side of the garment, extending longitudinally through the crotch region between the front and back regions, a removable absorbent pad of a size larger than the first size.

BRIEF DESCRIPTION OF THE DRAWINGS

The foregoing summary and the following detailed description will be better understood when read in conjunction with the appended drawings. For the purpose of illustrating the invention, there is shown in the drawings embodiments which are presently preferred. It should be understood, however, that the invention is not limited to the precise arrangements and instrumentality shown. In the drawings:

FIG. 1 is a plan view of a preferred embodiment crotch assembly for a garment in accordance with the present invention;

FIG. 3 depicts an intermediate stage of the assembly of FIG. 1; and

FIG. 4 depicts the assembly of FIGS. 1 through incorporated into a panty as a crotch panel.

DESCRIPTION OF THE PREFERRED EMBODIMENT

Figure 2:
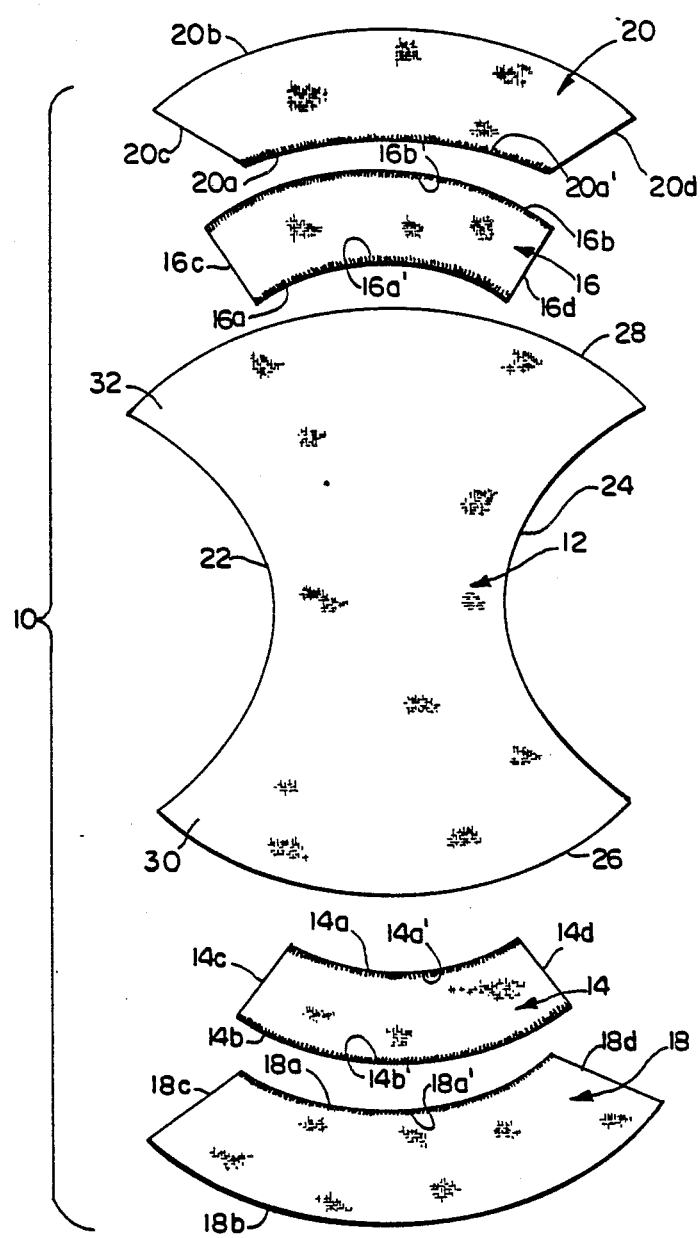
FIG. 2 depicts the individual components of the assembly of FIG. 1 before assembly.

Referring to the drawings, like numerals are employed for like elements throughout. FIG. 1 depicts a preferred crotch assembly for use in a garment as a panel or liner and indicated generally at 10. The individual components of the assembly 10 are depicted separately in FIG. 2. The assembly 10 includes a crotch piece 12, a first pair of front and rear inner ("mini") pocket panels 14 and 16, respectively, and a second pair of front and rear, outer ("maxi") pocket panels 18 and 20, respectively.

Preferably each of the pieces 12 through 2 is cut from a soft, woven cotton fabric for breathability and ease of cleaning. However, any other pliable fabric may be used. For example, nylon (about 40 denier) is often used in undergarment crotch construction.

Still referring to FIG. 2, the crotch piece 12 is preferably adapted for comfortable wearing in the user's crotch region by the provision of a pair of opposing bights, preferably in the form of opposing generally concave edges 22 and 24, respectively. Preferably, the assembly 10 is further adapted for attachment with other panel pieces for constructing an undergarment by the provision of a pair of front and rear opposing generally convex edges 26 and 28, extending between the concave edges 22 and 24 at the front and back ends 30 and 32, respectively, of crotch piece 12. Preferably, the first pair of inner pocket panels 14 and 16 are identical and interchangeable. Preferably, the second pair of panels 18 and 20 also are similarly identical and interchangeable. Preferably, each of the pocket panels 14 through 20 includes an inner, generally concave edge "a" and an opposing, generally concentric and convex, outer edge "b". Straight edges "c" and "d" extend between the concave and convex edges "a" and "b" of each panel 14-20. Preferably, the inner and outer edges 14a, 16a and 14b, 16b of the first pair of inner pocket panels 14 and 16, are rolled and overlocked by stitching indicated at 14a', 14b', 16a' and 16b'. Preferably, the inner edges 18a and 20a of the outer pair of pocket panels 18 and 20 are similarly rolled and overlocked with stitching 18a' and 20a', respectively.

FIG. 3 depicts an intermediate stage of construction of the assembly 10, noted as 10', in which the front and rear inner pocket panels 14 and 16 have been located and preferably permanently attached to one side ("inner" side) 13 of the crotch piece 12 by suitable means such as ZZ stitches 36 along their outer convex edges 14b and 16b, respectively. The ZZ stitches 36 stop short of the straight edges "c" and "d"(see FIG. 2). The front and back outer pocket panels 18 and 20 are then secured on the one side 13 of the crotch piece 12 (see FIG. 1) with their outer convex edges 18b and 20b approximately aligned with the convex edges 26 and 28, respectively, of the crotch piece 12 and their inner concave edges 18a and 20a overlapping convex edges 14b and 16b, respectively, of the inner pocket panels 14 and 16. For example, basting stitches 38 (see FIG. 1) may be provided to temporarily hold the outer pocket panels 18 and 20 to the crotch piece 12 until the assembly 10 can be used as a panel and combined with other panels and/or edgings to form a completed undergarment such as the panty 40 of FIG. 4 or other garment or combined with a garment as a crotch liner. The straight edges "c" and "d" of each of the panels 14–20 may be left unstitched, if desired, to receive edgings (not depicted). Although not depicted in the figures, at least the outer pocket panels 18 and 20 can be stitched substantially along their side edges "c" and "d" to leave their convex edges "b" and the convex edges 26 and 28 of the crotch piece 12 unattached to received adjoining edges of front and/or back panels of a garment into which the assembly 10 is incorporated. Other various temporary and permanent stitching arrangements will occur to those of ordinary skill depending upon the end use of the liner.

Referring to FIG. 4, the panty 40 includes, in addition to the crotch assembly 10, a front panel 42 and a rear panel 44 attached to the front and back ends 30 and 32, respectively, of the crotch piece 12 (see FIG. 2). The front and back panels 42 and 44 are joined by stitching in a conventional manner at their adjoining side edges to form a pair of opposing side seams 46 and 48. An elastic waistband 50 preferably is attached to the front and back panels, by suitable means such as appropriate stitching. Elastic cuffs 52 and 54 preferably are applied over the concave edges 22 and 24, respectively, of the crotch piece 12 and over curved edges of the front and back panels 42 and 44 which defines with the concave edges 22 and 24 of the crotch piece 12 a pair of leg openings 56 and 58, respectively. The same stitching used to secure the elastic cuffs 52 and 54 to the crotch piece 12 can be used to secure the remaining, straight edges "c" and "d" of each of the pocket panels 14 through 20 to the crotch piece 12, if not already secured, completing the construction of the pockets. The inner curved edge "a" of reach of the pocket panels 14 through 20 forms the one open side of each pocket formed by those panels with the crotch piece 12.

Referring to FIGS. 1 and 4, the inner pocket panels 14 and 16 form with the crotch piecer 12, a first pair of pockets which comprise an inner fabric means attached to the crotch piece 12 for receiving and retaining flush on the one side 13 of the crotch piece 12 a removable absorbent pad 60, indicated in phantom by a broken line, of up to a first size, such as a typical thin disposable sanitary panty liner. The outer pocket panels 18 and 20 form with the crotch piece 12, a second pair of pockets which comprise an outer fabric means attached to the crotch piece 12 for receiving and retaining flush on the one side 13, a removable absorbent pad 62, indicated in phantom by dot and dashed lines, of a size larger than the first size of pad 60. Pad 62 may be a full size disposable napkin or sanitary pad. Each pad 60 and 62 extends longitudinally between the concave edges 22 and 24 (FIG. 2) through the crotch region between the front and back portions of the panty 40 (FIG. 4), provided by front and back panels 42 and 44, respectively.

The inner pocket panels 14 and 16 are spaced apart a sufficient distance on the crotch piece 12 to receive and retain opposite ends of the first size pad 60 while the inner and outer, panels 18 and 20 are spaced apart a greater distance to receive the larger size pads 62. The inner and outer panels 14–20 each may be, for example, at least about one-and-one-half inches long between their inner edge ("a") and their outer edge ("b"). The inner edges "a" of the inner pair of pockets formed by the inner panels 14 and 16 may be, for example, spaced about three inches apart along the concave edges 22 and 24 of the crotch piece 12. The inner edges "a" of the outer pockets formed by the outer pocket panels 18 and 20 may be, for example, about five inches apart along the concave edges 22 and 24 of the crotch piece 12. The inner edges "a" of the outer fabric means pockets, formed by the outer pocket panels 18 and 20, thus overlap the outer edges "b" of the inner fabric means pockets, formed by the inner pocket panels 14 and 16, respectively. Provision of the inner and outer fabric means pockets allows either of two different sized pads to be received and stationarily held without movement of the smaller sized pad 60 or bunching of the larger sized pad 62. With the curvature, length and spacing of the inner panels 14 and 16, forming the inner fabric means, a pad at least about six inches long can be received and held flushly to the crotch piece 12. With the curvature, length and spacing of the outer panels 18 and 20 forming the outer fabric means, a pad at least about seven inches long can be received and held flushly to the crotch piece 12.

The invention is intended to encompass any garment which may be worn in direct contact with the crotch area and which incorporates the inner and outer fabric means for receiving and retaining removable absorbent pads of either a first size or a larger size on an inner side of the garment by the provision of inner and outer pairs of pockets or equivalent means. The invention is further intended to cover garments which do not include an individual crotch panel or, if a crotch panel is provided, one which does not directly receive and support the inner and outer pockets or equivalent inner and/or outer fabric means.

Furthermore, the invention is intended to cover the use of the crotch assembly 10 as a liner which is positioned in or secured to the inner side of a fully-formed garment having a separate, finished crotch region.

From the foregoing description, it can be seen that the present invention provides a crotch assembly which can be readily attached by conventional means such as sewing to other elements to fabricate various crotch-contacting garments such as panties, underpants, panty hose, girdles, panty girdles, teddies, swimsuits, trunks, leotards, thermal underwear and the like.

The present invention provides an means for comfortably holding removable pads, particularly disposable sanitary pads and panty liners, of various sizes in place and in such a fashion that they do not bunch up, "bulk" or slide out of place in use.

Another advantage of the preferred embodiment of the invention is that the supporting device is effective yet breathable and washable.

Yet another advantage of the preferred embodiment of the invention is that the retaining means contain no abrasive, scratchy, cutting or otherwise irritating surfaces or edges. Garments provided with the present invention can continue to be comfortably worn even when removable pads are not being used by the wearer.

It will be recognized by those skilled in the art that changes could be made to the above-described embodiments of the invention without departing from the broad, inventive concepts thereof. It is understood, therefore, that the invention is not limited to the particular embodiments disclosed or suggested but is intended to cover any modifications which are within the scope and spirit of the invention, as are defined by the appended claims.

I claim:

1. A crotch assembly for a garment comprising:
   a fabric crotch piece having a pair of opposing sides defined in part by a part of longitudinally extending, opposing, generally concave edges;
   inner fabric means on one side of the crotch piece attached to the crotch piece for receiving and retaining a generally elongated, removable absorbent pad of up to only a first length flush on the one side of the crotch piece, extending longitudinally along the crotch piece between the concave edges; and
   outer fabric means on the one side of the crotch piece attached to the crotch piece for receiving and retaining a generally elongated, removable absorbent pad of a length longer than the first length flush on the one side of the crotch piece, extending longitudinally along the crotch piece between the concave edges, at least one of the inner and outer fabric means comprising a pair of pockets on the one side of the crotch piece, each pocket of the pair extending generally between the concave edges of the crotch piece and each pocket of the pair having an open side facing the remaining pocket of the pair.

2. The crotch assembly of claim 1 wherein each of the inner fabric means and the outer fabric means comprises a pair of pockets on the one side of the crotch piece, each pocket of each pair extending generally between the concave edges of the crotch piece and each pocket of each pair having an open side facing the remaining pocket of the pair.

3. The crotch assembly of claim 2 wherein each of the pockets is formed by a separate flat panel attached to the one side of the crotch piece.

4. The crotch assembly of claim 3 wherein the crotch piece and each flat panel forming one of the pockets is a piece of cotton fabric.

5. The crotch assembly of claim 3 wherein each of the flat panels has a concave inner edge and a convex outer edge and wherein the concave inner edge of each of the flat panels forming the outer fabric means pair of pockets overlaps the outer convex edge of one of the flat panels forming the inner fabric means pair of pockets.

6. The crotch assembly of claim 1 wherein the crotch piece has a pair of opposing generally convex edges, each of the convex edges extending between the concave edges of the crotch piece.

7. In a garment including a waistband, a crotch region and front and back regions extending from the crotch region to the waistband, the improvement comprising:
   inner fabric means fixedly secured to the garment for receiving and retaining a generally elongated, removable absorbent pad of up to only a first length flush on an inner side of the garment extending longitudinally through the crotch region between the front and back regions; and
   outer fabric means fixedly secured to the undergarment for receiving and retaining a generally elongated, removable absorbent pad of a length longer than the first length flush on the inner side of the garment extending longitudinally through the crotch region between the front and back regions, at least one of the inner and outer fabric means comprising a pair of pockets on the inner side of the garment in the crotch region, each pocket of the pair extending generally across a portion of the crotch region and each pocket of the pair having an open side facing the remaining pocket of the pair.

8. The improvement of claim 7 wherein the inner fabric means comprises an inner pair of facing pockets on the inner side of the garment and the outer fabric means comprises an outer pair of facing pockets on the inner side of the garment.

9. The garment of claim 8 comprising a crotch panel including a crotch piece and a plurality of flat fabric panels attached to the crotch piece and forming with the crotch piece the inner pair and the outer pair of facing pockets on one side of the crotch panel forming the inner side of the crotch region of the garment.

* * * * *